United States Patent
Lawson et al.

(10) Patent No.: US 8,664,468 B2
(45) Date of Patent: Mar. 4, 2014

(54) DISPOSABLE ABSORBENT ARTICLES HAVING AN INTERIOR DESIGN SIGNAL

(75) Inventors: Kathleen Marie Lawson, West Chester, OH (US); Mark John Ciesko, Cincinnati, OH (US); Christofer Fuchs, Wyoming, OH (US); Alizha Victoria Rice, Cincinnati, OH (US); Harald Hermann Hundorf, Bonn (DE); Horst Blessing, Euskirchen (DE); Peter Dziezok, Hochheim (DE); Mattias Schmidt, Idstein (DE); Holger Beruda, Schwalbach (DE); Bruno Johannes Ehrnsperger, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/562,353

(22) Filed: Jul. 31, 2012

(65) Prior Publication Data
US 2012/0296301 A1 Nov. 22, 2012

Related U.S. Application Data

(62) Division of application No. 11/942,999, filed on Nov. 20, 2007, now Pat. No. 8,258,367.

(60) Provisional application No. 60/861,909, filed on Nov. 29, 2006.

(51) Int. Cl.
*A61F 13/15* (2006.01)

(52) U.S. Cl.
USPC .......................................... 604/361

(58) Field of Classification Search
USPC ......... 604/358, 361, 366, 368, 370, 372, 378, 604/385.01
See application file for complete search history.

(56) References Cited

U.S. PATENT DOCUMENTS

| 3,860,003 | A | 1/1975 | Buell |
| 4,055,180 | A | 10/1977 | Karami |
| 4,079,739 | A | 3/1978 | Whitehead |

(Continued)

FOREIGN PATENT DOCUMENTS

| CN | 1371671 A | 2/2001 |
| EP | 0 394 274 B2 | 7/1996 |

(Continued)

OTHER PUBLICATIONS

Definition of "undulate", Merriam-Webster OnLine.

*Primary Examiner* — Melanie Hand
(74) *Attorney, Agent, or Firm* — Laura L. Whitmer

(57) ABSTRACT

Disposable absorbent article comprising an interior design signal indicating absorbency and an absorbent core including first and second absorbent layers, the first absorbent layer including a first substrate and the second absorbent layer including a second substrate, the first and second absorbent layers further including absorbent particulate polymer material deposited on the first and second substrates and thermoplastic material covering the absorbent particulate polymer material on the respective first and second substrates, the first and second absorbent layers combined together such that at least a portion of the thermoplastic material of the first absorbent layer contacts at least a portion of the thermoplastic material of the second absorbent layer, the absorbent particulate polymer material is disposed between the first and second substrates in an absorbent particulate polymer material area, and the absorbent particulate polymer material is substantially continuously distributed across the absorbent particulate polymer material area.

14 Claims, 6 Drawing Sheets

(56) References Cited

U.S. PATENT DOCUMENTS

| | | |
|---|---|---|
| 4,360,021 A | 11/1982 | Stima |
| 4,381,783 A | 5/1983 | Elias |
| 4,410,571 A | 10/1983 | Korpman |
| 4,573,986 A | 3/1986 | Minetola et al. |
| 4,610,678 A | 9/1986 | Weisman et al. |
| 4,806,598 A | 2/1989 | Morman |
| 4,826,880 A | 5/1989 | Lesniak et al. |
| 4,834,735 A | 5/1989 | Alemany et al. |
| 4,888,231 A | 12/1989 | Angstadt |
| 4,940,464 A | 7/1990 | VanGompel et al. |
| 4,966,809 A | 10/1990 | Tanaka et al. |
| 4,994,053 A | 2/1991 | Lang |
| 5,037,416 A | 8/1991 | Allen et al. |
| 5,092,861 A | 3/1992 | Nomura et al. |
| 5,151,092 A | 9/1992 | Buell et al. |
| 5,246,433 A | 9/1993 | Hasse et al. |
| 5,248,309 A | 9/1993 | Serbiak et al. |
| 5,260,345 A | 11/1993 | DesMarais et al. |
| 5,269,775 A | 12/1993 | Freeland et al. |
| 5,382,610 A | 1/1995 | Harada et al. |
| 5,387,207 A | 2/1995 | Dyer et al. |
| 5,387,208 A | 2/1995 | Ashton et al. |
| 5,397,316 A | 3/1995 | LaVon et al. |
| 5,397,317 A | 3/1995 | Thomas |
| 5,429,630 A | 7/1995 | Beal et al. |
| 5,460,622 A | 10/1995 | Dragoo et al. |
| 5,486,167 A | 1/1996 | Dragoo et al. |
| 5,554,145 A | 9/1996 | Roe et al. |
| 5,559,335 A | 9/1996 | Zing et al. |
| 5,562,646 A | 10/1996 | Goldman et al. |
| 5,569,234 A | 10/1996 | Buell et al. |
| 5,571,096 A | 11/1996 | Dobrin et al. |
| 5,586,979 A | 12/1996 | Thomas |
| 5,601,542 A | 2/1997 | Melius et al. |
| 5,625,222 A | 4/1997 | Yoneda |
| 5,669,894 A | 9/1997 | Goldman et al. |
| 5,833,678 A | 11/1998 | Ashton et al. |
| 5,840,404 A | 11/1998 | Graff |
| 5,897,545 A | 4/1999 | Kline et al. |
| 5,941,862 A | 8/1999 | Haynes et al. |
| 5,957,908 A | 9/1999 | Kline et al. |
| 6,004,306 A | 12/1999 | Robles et al. |
| 6,120,487 A | 9/2000 | Ashton |
| 6,120,489 A | 9/2000 | Johnson et al. |
| 6,319,239 B1 | 11/2001 | Daniels et al. |
| 6,416,502 B1 | 7/2002 | Connelly et al. |
| 7,163,528 B2 | 1/2007 | Christon et al. |
| 7,241,280 B2 | 7/2007 | Christen et al. |
| 7,270,651 B2 | 9/2007 | Adams et al. |
| 7,306,582 B2 | 12/2007 | Adams et al. |
| 7,311,696 B2 | 12/2007 | Christen et al. |
| 8,167,862 B2 * | 5/2012 | Digiacomantonio et al. ............ 604/385.201 |
| 2002/0058919 A1 | 5/2002 | Hamilton et al. |
| 2003/0109839 A1 | 6/2003 | Costae et al. |
| 2003/0114811 A1 | 6/2003 | Christen et al. |
| 2003/0233082 A1 | 12/2003 | Kline et al. |
| 2004/0162536 A1 | 8/2004 | Becker et al. |
| 2004/0167486 A1 | 8/2004 | Busam et al. |
| 2004/0170813 A1 | 9/2004 | Digiacomantonio et al. |
| 2007/0191798 A1 | 8/2007 | Glaug et al. |
| 2008/0132864 A1 | 6/2008 | Lawson et al. |

FOREIGN PATENT DOCUMENTS

| | | |
|---|---|---|
| EP | 0 737 055 B1 | 8/1998 |
| EP | 0 875 224 A1 | 11/1998 |
| EP | 0 724 418 B1 | 3/1999 |
| EP | 0 725 613 B1 | 3/1999 |
| EP | 0 725 616 B1 | 3/1999 |
| EP | 0 778 762 B1 | 4/2000 |
| EP | 0 796 068 B1 | 5/2001 |
| EP | 1116479 A2 | 7/2001 |
| EP | 0 790 839 B1 | 8/2001 |
| EP | 0 737 056 B2 | 1/2003 |
| JP | 2003-126140 A | 5/2003 |
| JP | 2006-513824 T | 4/2006 |
| WO | WO 95/16746 | 6/1995 |
| WO | WO 95/26209 | 10/1995 |
| WO | WO 2006/062258 A3 | 6/2006 |

* cited by examiner

DISPOSABLE ABSORBENT ARTICLES HAVING AN INTERIOR DESIGN SIGNAL

CROSS REFERENCE TO RELATED APPLICATION

This application is a divisional of U.S. application Ser. No. 11/942,999, filed Nov. 20, 2007, now U.S. Pat. No. 8,258,367 which claims the benefit of U.S. Provisional Application No. 60/861,909, filed Nov. 29, 2006, the substance of which is incorporated herein by reference.

FIELD

In general, embodiments of the present disclosure relate to disposable absorbent articles. In particular, embodiments of the present disclosure relate to disposable absorbent articles having an interior design signal.

BACKGROUND

Disposable absorbent articles include disposable diapers, disposable feminine hygiene products, and disposable incontinence undergarments. A disposable absorbent article can receive and contain bodily waste while being worn by a wearer. Such articles can be made with various materials in a number of configurations. Multiple attempts have been made to provide them with an overall good fit and with a high absorbent capacity. Modern diapers make use of absorbent materials, which allow for storage of large amounts of liquid in thinner absorbent articles.

U.S. Patent Application No. 2004/0162536 discloses an absorbent core for an absorbent article that provides an improved immobilization of absorbent polymer material when the article is fully or partially urine loaded. The absorbent core is useful for providing an absorbent article having increased wearing comfort.

U.S. Patent Application No. 2004/0167486 discloses an absorbent core for an absorbent article that provides increased wearing comfort to the article and makes it thin and dry.

While the aforementioned applications describe an absorbent article having an improved fit and a thinner appearance, a need still exists for a mechanism to communicate to the caregiver that a thinner absorbent article is still useful for providing absorbency.

SUMMARY

The present invention is directed to a disposable absorbent article comprising an interior design signal indicating absorbency and an absorbent core including first and second absorbent layers, the first absorbent layer including a first substrate and the second absorbent layer including a second substrate, the first and second absorbent layers further including absorbent particulate polymer material deposited on the first and second substrates and thermoplastic material covering the absorbent particulate polymer material on the respective first and second substrates, the first and second absorbent layers combined together such that at least a portion of the thermoplastic material of the first absorbent layer contacts at least a portion of the thermoplastic material of the second absorbent layer, the absorbent particulate polymer material is disposed between the first and second substrates in an absorbent particulate polymer material area, and the absorbent particulate polymer material is substantially continuously distributed across the absorbent particulate polymer material area.

Alternatively, the present invention is directed to a disposable absorbent article comprising an interior design signal indicating absorbency and an absorbent core including a first absorbent layer, the first absorbent layer including a first substrate, absorbent particulate polymer material deposited on the first substrate, and thermoplastic material covering the absorbent particulate polymer material on the first substrate, the absorbent particulate polymer material is substantially continuously distributed across the absorbent particulate polymer material area.

DETAILED DESCRIPTION

Figure 1:
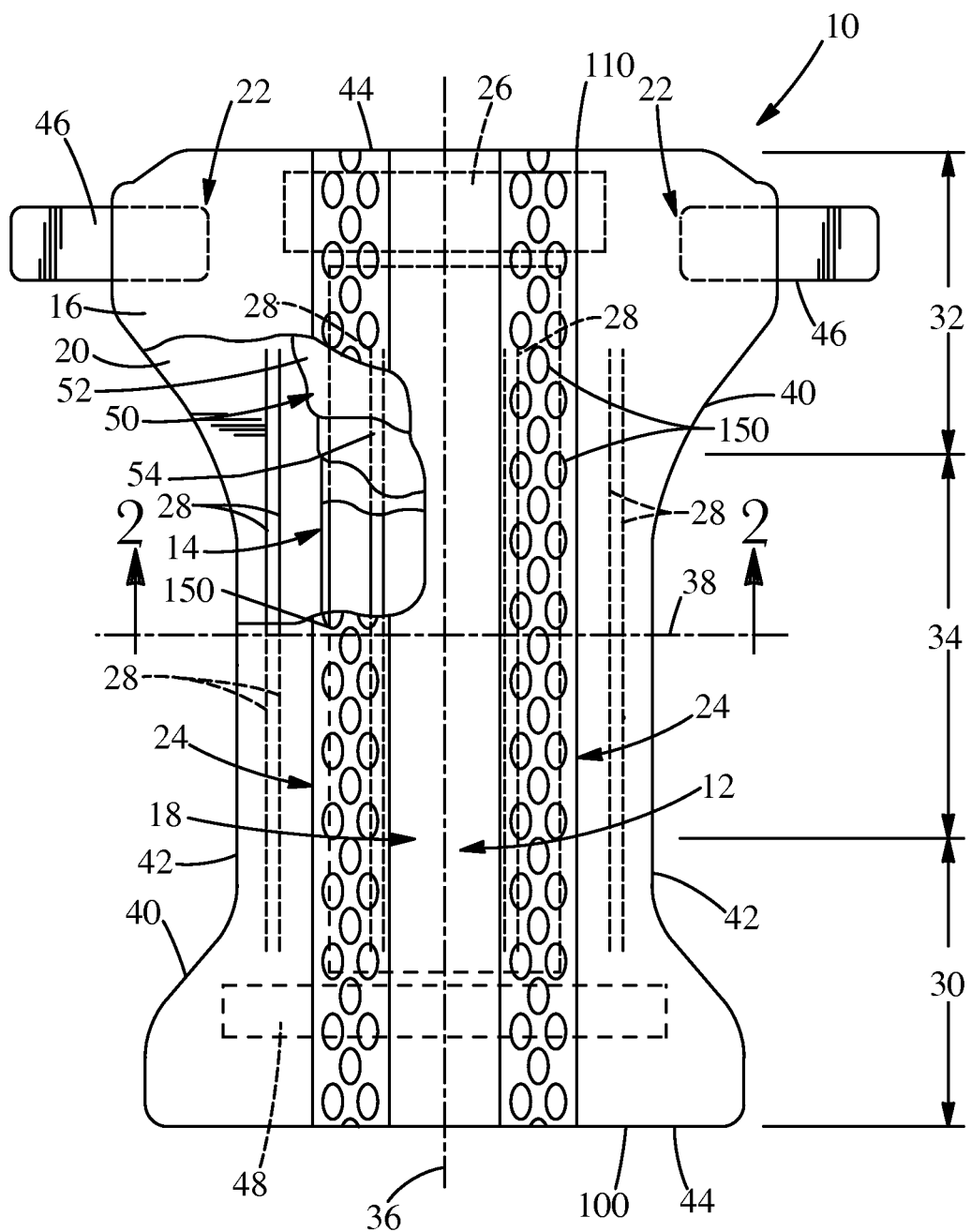
FIG. 1 is a plan view of a diaper in accordance with an embodiment of the present invention.

The present invention concerns an absorbent article, preferably a disposable absorbent article, such as a diaper.

As used herein, the following terms have the following meanings:

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure typically disposed between a top sheet and cover sheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core may be substantially cellulose free. The absorbent core does not include an acquisition system, a top sheet, or a back sheet of the absorbent article. In a certain embodiment, the absorbent core would consist essentially of the one or more substrates, the absorbent polymer material, the thermoplastic composition, and optionally the cover layer.

"Airfelt" is used herein to refer to comminuted wood pulp, which is a form of cellulosic fiber.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Fiber" and "filament" are used interchangeably.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed", as used herein, refers to absorbent particulate polymer material that is arranged across the absorbent particulate polymer material area. Optionally, the absorbent particulate polymer material may be arranged such that the substrate layers do not touch in various zones. In one embodiment, the substrate layers may touch in the peripheral areas outside the absorbent particulate polymer material area. It is important to note that the thermoplastic material used in the present invention does not interrupt the substantially continuously distributed absorbent particulate polymer material. Thus, the substantially continuously distributed absorbent particulate polymer material includes the thermoplastic material.

"Thickness" and "caliper" are used herein interchangeably.

FIG. 1 is a plan view of a diaper 10 according to a certain embodiment of the present invention. The diaper 10 is shown in its flat out, uncontracted state (i.e., without elastic induced contraction) and portions of the diaper 10 are cut away to more clearly show the underlying structure of the diaper 10. A portion of the diaper 10 that contacts a wearer is facing the viewer in FIG. 1. The diaper 10 generally may comprise a chassis 12 and an absorbent core 14 disposed in the chassis.

The chassis 12 of the diaper 10 in FIG. 1 may comprise the main body of the diaper 10. The chassis 12 may comprise an outer covering 16 including a top sheet 18, which may be liquid pervious, and/or a back sheet 20, which may be liquid impervious. The absorbent core 14 may be encased between the top sheet 18 and the back sheet 20. The chassis 12 may also include side panels 22, elasticized leg cuffs 24, and an elastic waist feature 26.

The leg cuffs 24 and the elastic waist feature 26 may each typically comprise elastic members 28. One end portion of the diaper 10 may be configured as a first waist region 30 of the diaper 10. The first waist region 30 has a first edge 100. An opposite end portion of the diaper 10 may be configured as a second waist region 32 of the diaper 10. The second waist region 32 has a second edge 110. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with its longitudinal axis 36 and its transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastening member 46 and at least one stored landing zone 48.

The diaper 20 may also include such other features as are known in the art including front and rear ear panels, waist cap features, elastics and the like to provide better fit, containment and aesthetic characteristics. Such additional features are well known in the art and are e.g., described in U.S. Pat. No. 3,860,003 and U.S. Pat. No. 5,151,092.

In order to keep the diaper 10 in place about the wearer, at least a portion of the first waist region 30 may be attached by the fastening member 46 to at least a portion of the second waist region 32 to form leg opening(s) and an article waist. When fastened, the fastening system carries a tensile load around the article waist. The fastening system may allow an article user to hold one element of the fastening system, such as the fastening member 46, and connect the first waist region 30 to the second waist region 32 in at least two places. This may be achieved through manipulation of bond strengths between the fastening device elements.

According to certain embodiments, the diaper 10 may be provided with a re-closable fastening system or may alternatively provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven webs, woven webs, paper, laminates, fiber reinforced plastics and the like, or combinations thereof. In certain embodiments, the materials making up the fastening device may be flexible. The flexibility may allow the fastening system to conform to the shape of the body and thus, reduce the likelihood that the fastening system will irritate or injure the wearer's skin.

For unitary absorbent articles, the chassis 12 and absorbent core 14 may form the main structure of the diaper 10 with other features added to form the composite diaper structure. While the top sheet 18, the back sheet 20, and the absorbent core 14 may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The top sheet 18 in FIG. 1 may be fully or partially elasticized or may be foreshortened to provide a void space between the top sheet 18 and the absorbent core 14. Exemplary structures including elasticized or foreshortened top sheets are described in more detail in U.S. Pat. No. 5,037,416 entitled "Disposable Absorbent Article Having Elastically Extensible Top sheet" issued to Allen et al. on Aug. 6, 1991; and U.S. Pat. No. 5,269,775 entitled "Trisection Top sheets for Disposable Absorbent Articles and Disposable Absorbent Articles Having Such Trisection Top sheets" issued to Freeland et al. on Dec. 14, 1993.

The back sheet 26 may be joined with the top sheet 18. The back sheet 20 may prevent the exudates absorbed by the absorbent core 14 and contained within the diaper 10 from soiling other external articles that may contact the diaper 10, such as bed sheets and undergarments. In certain embodiments, the back sheet 26 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable back sheet films include those manufactured by Tredegar Industries Inc. of Terre Haute, Ind. and sold under the trade names X15306, X10962, and X10964. Other suitable back sheet materials may include breathable materials that permit vapors to escape from the diaper 10 while still preventing exudates from passing through the back sheet 10. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E.I. DuPont. Other breathable back sheets including nonwoven webs and apertured formed films are described in U.S. Pat. No. 5,571,096 issued to Dobrin et al. on Nov. 5, 1996.

Figure 2:
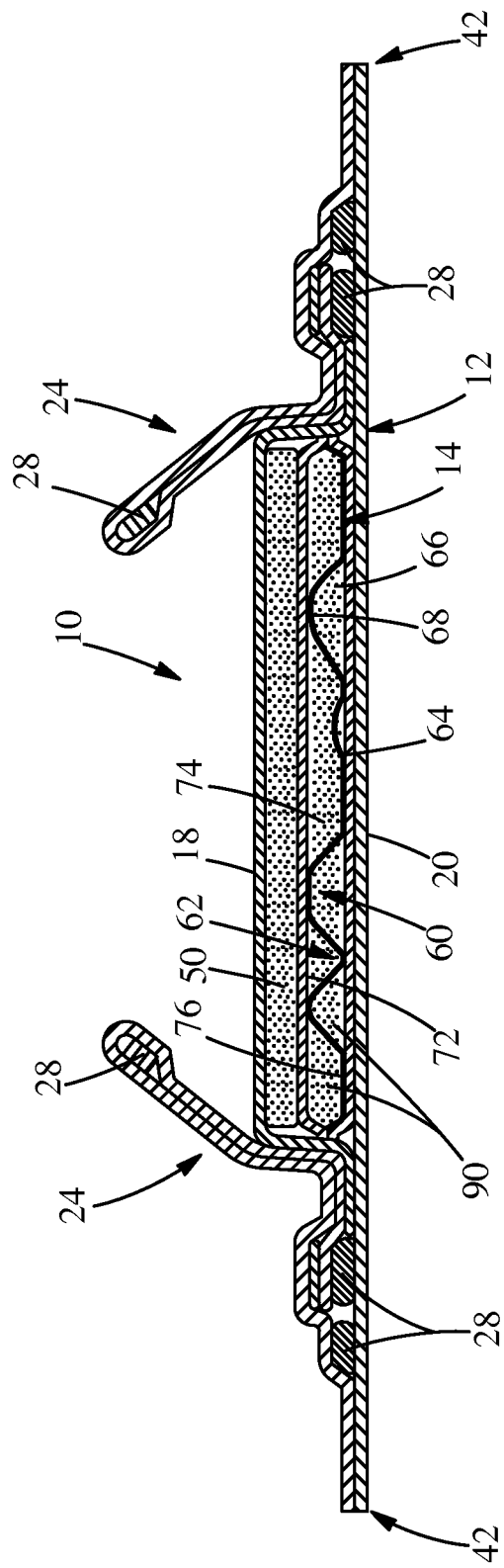
FIG. 2 is a cross sectional view of the diaper shown in FIG. 1 taken along the sectional line 2-2 of FIG. 1.

FIG. 2 shows a cross section of FIG. 1 taken along the sectional line 2-2 of FIG. 1. Starting from the wearer facing side, the diaper 10 may comprise the top sheet 18, the components of the absorbent core 14, and the back sheet 20. According to a certain embodiment, diaper 10 may also comprise an acquisition system 50 disposed between the liquid permeable top sheet 18 and a wearer facing side of the absorbent core 14. The acquisition system 50 may be in direct contact with the absorbent core. The acquisition system 50 may comprise a single layer or multiple layers, such as an upper acquisition layer 52 facing the towards the wearer's skin and a lower acquisition 54 layer facing the garment of the wearer. According to a certain embodiment, the acquisition system 50 may function to receive a surge of liquid, such as a gush of urine, and quickly absorb the liquid and distribute it across the absorbent core 14 so that the absorbent core absorbs the liquid before the liquid flows beyond the absorbent layer 14 and out of the diaper 10. In other words, the acquisition system 50 may serve as a temporary reservoir for liquid until the absorbent core 14 can absorb the liquid.

Figure 3:
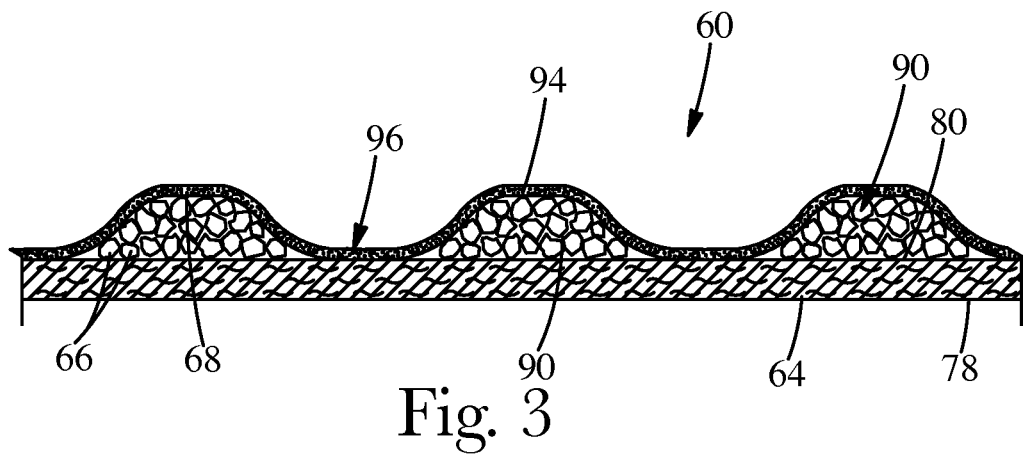
FIG. 3 is a partial cross sectional view of an absorbent core layer in accordance with an embodiment of this invention.

The absorbent core 14 is disposed between the top sheet 18 and the back sheet 20 and comprises two layers, a first absorbent layer 60 and a second absorbent layer 62. As shown in FIG. 3, the first absorbent layer 60 of the absorbent core 14 comprises a substrate 64, an absorbent particular polymer material 66 on the substrate 64, and a thermoplastic composition 68 on the absorbent particulate polymer material 66 and at least portions of the first substrate 64 as an adhesive for covering and immobilizing the absorbent particulate polymer material 66 on the first substrate 64. According to another embodiment, the first absorbent layer 60 of the absorbent core 14 may also include a cover layer on the thermoplastic composition 68.

Likewise, as illustrated in FIG. 2, the second absorbent layer 62 of the absorbent core 14 may also include a substrate 72, an absorbent particulate polymer material 74 on the second substrate 72, and a thermoplastic composition 66 on the absorbent particulate polymer material 74 and at least a portion of the second substrate 72 for immobilizing the absorbent particulate polymer material 74 on the second substrate 72. Although not illustrated, the second absorbent layer 62 may also include a cover layer such as the cover layer.

The substrate 64 of the first absorbent layer 60 may be referred to as a dusting layer and has a first surface 78 which faces the back sheet 20 of the diaper 10 and a second surface 80 which faces the absorbent particulate polymer material 66. Likewise, the substrate 72 of the second absorbent layer 62 may be referred to as a core cover and has a first surface 82 facing the top sheet 18 of the diaper 10 and a second surface 84 facing the absorbent particulate polymer material 74. The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

According to a certain embodiment, the substrates 64 and 72 of the first and second absorbent layers 60 and 62 may be a non-woven material. In certain embodiments, the non-wovens are porous and in one embodiment has a pore size of about 32 microns.

Figure 4A:
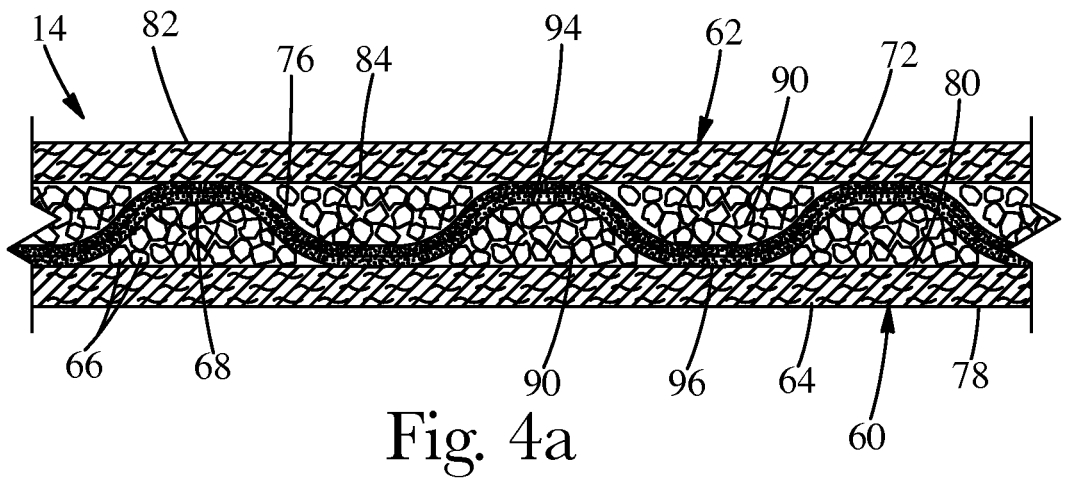
FIG. 4a is a partial sectional view of an absorbent core comprising a combination of the first and second absorbent core layers.
Figure 4B:
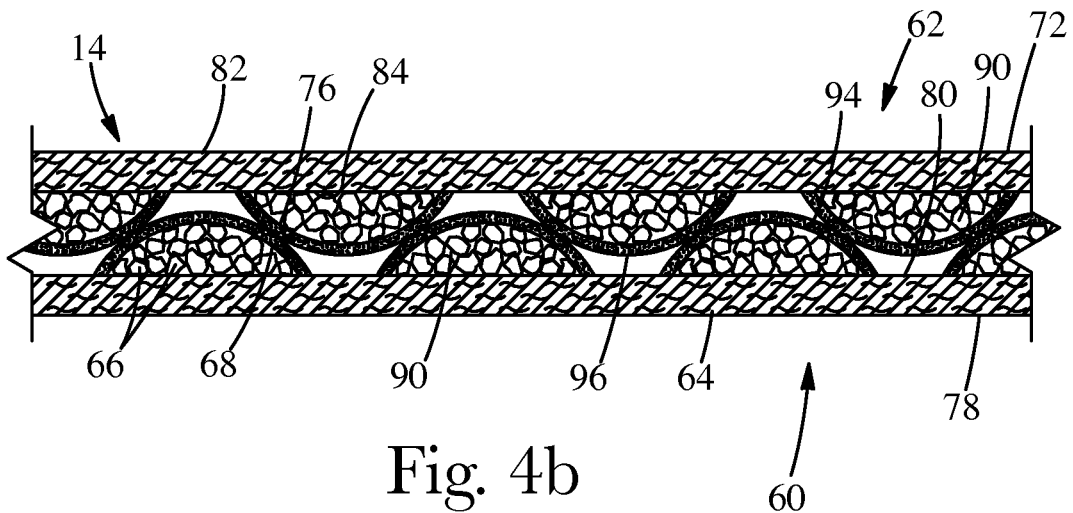
FIG. 4b is a partial sectional view of an absorbent core comprising a combination of the first and second absorbent core layers.

As illustrated in FIGS. 3, 4a, and 4b, the absorbent particulate polymer material 66 and 74 is deposited on the respective substrates 64 and 72 of the first and second absorbent layers 60 and 62 in clusters 90 of particles to form a grid pattern comprising land areas 94 and junction areas 96 between the land areas 94. The junction areas 96 in the grid pattern contain little or no absorbent particulate polymer material 66 and 74. The land areas 94 and junction areas 96 can have a variety of shapes including, but not limited to, circular, oval, square, rectangular, triangular, and the like.

The first and second absorbent layers 60 and 62 may be combined together to form the absorbent core 14 such that the grid patterns of the respective first and second absorbent layers 62 and 64 are offset from one another along the length and/or width of the absorbent core 14. The respective grid patterns may be offset such that the absorbent particulate polymer material 66 and 74 is substantially continuously distributed across the absorbent particulate polymer area. In a certain embodiment, absorbent particulate polymer material 66 and 74 is substantially continuously distributed across the absorbent particulate polymer material area despite the individual grid patterns comprising absorbent particulate polymer material 66 and 74 discontinuously distributed across the first and second substrates 64 and 72 in clusters. In a certain embodiment, the grid patterns may be offset such that the land areas 94 of the first absorbent layer 60 face the junction areas 96 of the second absorbent layer 62 and the land areas 94 of the second absorbent layer 62 face the junction areas 96 of the first absorbent layer 60. When the land areas 94 and junction areas 96 are appropriately sized and arranged, the resulting combination of absorbent particulate polymer material 66 and 74 is a substantially continuous layer of absorbent particular polymer material across the absorbent particulate polymer material area of the absorbent core 14. In a certain embodiment, respective grid patterns of the first and second absorbent layer 60 and 62 may be substantially the same.

In a certain embodiment, the amount of absorbent particulate polymer material 66 and 74 may vary along the length of the grid pattern. In a certain embodiment, the grid pattern may be divided into any number of zones, in which the amount of absorbent particulate polymer material 66 and 74 varies from zone to zone. The amount of absorbent particulate polymer material 66 and 74 may, in a certain embodiment, gradually transition from one of the plurality of absorbent zones to another. This gradual transition in amount of absorbent particulate polymer material 66 and 74 may reduce the possibility of cracks forming in the absorbent core 14.

The amount of absorbent particulate polymer material 66 and 74 present in the absorbent core 14 may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In a particular embodiment, the absorbent core 14 consists essentially of the first and second substrates 64 and 72, the absorbent particulate polymer material 66 and 74, and the thermoplastic adhesive composition 68 and 76. In an embodiment, the absorbent core 14 may be substantially cellulose free.

In certain embodiments which are not substantially cellulose free, the absorbent core 14 can include some amount of cellulose fiber material, such as airfelt. A relatively low amount of cellulosic material is used, in certain embodiments, less than 40 weight percent, or 20 weight percent of cellulosic material, as compared to the weight of absorbent core.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

The thermoplastic material 68 and 76 may serve to cover and at least partially immobilize the absorbent particulate polymer material 66 and 74. In one embodiment of the present invention, the thermoplastic material 68 and 76 can be disposed essentially uniformly within the absorbent particulate polymer material 66 and 74. However, in a certain embodiment, the thermoplastic material 68 and 76 may be provided as a fibrous layer which is at least partially in contact with the absorbent particulate polymer material 66 and 74 and partially in contact with the substrate layers 64 and 72 of the first and second absorbent layers 60 and 62. FIGS. 3, 4a, and 4b show such a structure, and in that structure, the absorbent particulate polymer material 66 and 74 is provided as a discontinuous layer, and a layer of fibrous thermoplastic material 68 and 76 is laid down onto the layer of absorbent particulate polymer material 66 and 74, such that the thermoplastic material 68 and 76 is in direct contact with the absorbent particulate polymer material 66 and 74, but also in direct contact with the second surfaces 80 and 84 of the substrates 64 and 72, where the substrates are not covered by the absorbent particulate polymer material 66 and 74. This imparts an essentially three-dimensional structure to the fibrous layer of thermoplastic material 68 and 76, which in itself is essentially a two-dimensional structure of relatively small thickness, as compared to the extension in length and width directions. In other words, the thermoplastic material 68 and 76 undulates between the absorbent particulate polymer material 68 and 76 and the second surfaces of the substrates 64 and 72.

According to certain embodiments, the thermoplastic material 68 and 76 can comprise any thermoplastic material, including, but not limited to adhesive thermoplastic materials, also referred to as hot melt adhesives. Some initially thermoplastic materials may later lose their thermoplasticity due to a curing step, e.g., initiated via heat, UV radiation, electron beam exposure or moisture or other means of curing, leading to the irreversible formation of a crosslinked network of covalent bonds. Those materials having lost their initial thermoplastic behavior are herein also understood as thermoplastic materials.

Alternatively, the absorbent core of the present invention may include only one layer. In such an embodiment, the absorbent core includes a first absorbent layer, the first absorbent layer including a first substrate, absorbent particulate polymer material deposited on the first substrate, and thermoplastic material covering the absorbent particulate polymer material on the first substrate, the absorbent particulate polymer material is substantially continuously distributed across the absorbent particulate polymer material area. Alternatively, the first absorbent layer may include a second substrate.

In addition, the absorbent material may be immobilized when wet such that the absorbent core achieves a wet immobilization of more than about 50%, more than about 60%, more than about 70%, more than about 80%, more than about 90% according to the Wet Immobilization Test described herein.

Embodiments of the present invention include disposable absorbent articles having an interior design signal. As described above, absorbent cores are becoming increasingly thinner as technology advances, and the overall absorbent article is also becoming thinner. Caregivers typically associate thicker absorbent articles as being more absorbent than thinner ones. Thus, the present invention is directed to thinner absorbent articles, as descried in the embodiments discussed above, that have absorbency that is parity to thicker absorbent articles. Caregivers may benefit from a signal that thin absorbent articles will still provide absorbency similar to that of thicker absorbent articles. Utilizing a layer with a design signal is one way to indicate to the caregiver that the article will provide adequate absorbency protection, even when the article comprises a thinner absorbent core or is a thinner absorbent article. The interior design signals of the present invention may provide reassurance of improved performance, faster absorption, freshness, breathability, and skin dryness.

Utilizing a layer with a design cue supports the product functionality and strengthens trust and believability in the proposition that a thinner absorbent article may still be absorbent. The interior design signal may be located on the topsheet of the absorbent article. Alternatively, the interior design signal may be located on any layer beneath the topsheet, so long as a caregiver can see the signal prior to use. Thus, when the caregiver prepares the absorbent article to place it on the child, the signal is evident prior to use and instills confidence in the caregiver that the thin absorbent article will be as absorbent as thicker ones. Alternatively, the interior design signal may be located on the leg cuffs, as signals on the cuffs may also signal absorbency. Having the signal on the inside of the diaper, close to the child is an important tool in indicating absorbency to the caregiver.

The interior design signal may be created by patterns or shapes, solid colors, or mechanical modification of the absorbent article. First, caregivers may associate patterns, and/or shapes as an indication that the article will have improved product performance by better absorption and distribution. The interior design signals may indicate absorption channels that will distribute the liquid and absorb faster, indicating that a thinner article can work.

Figure 5A:
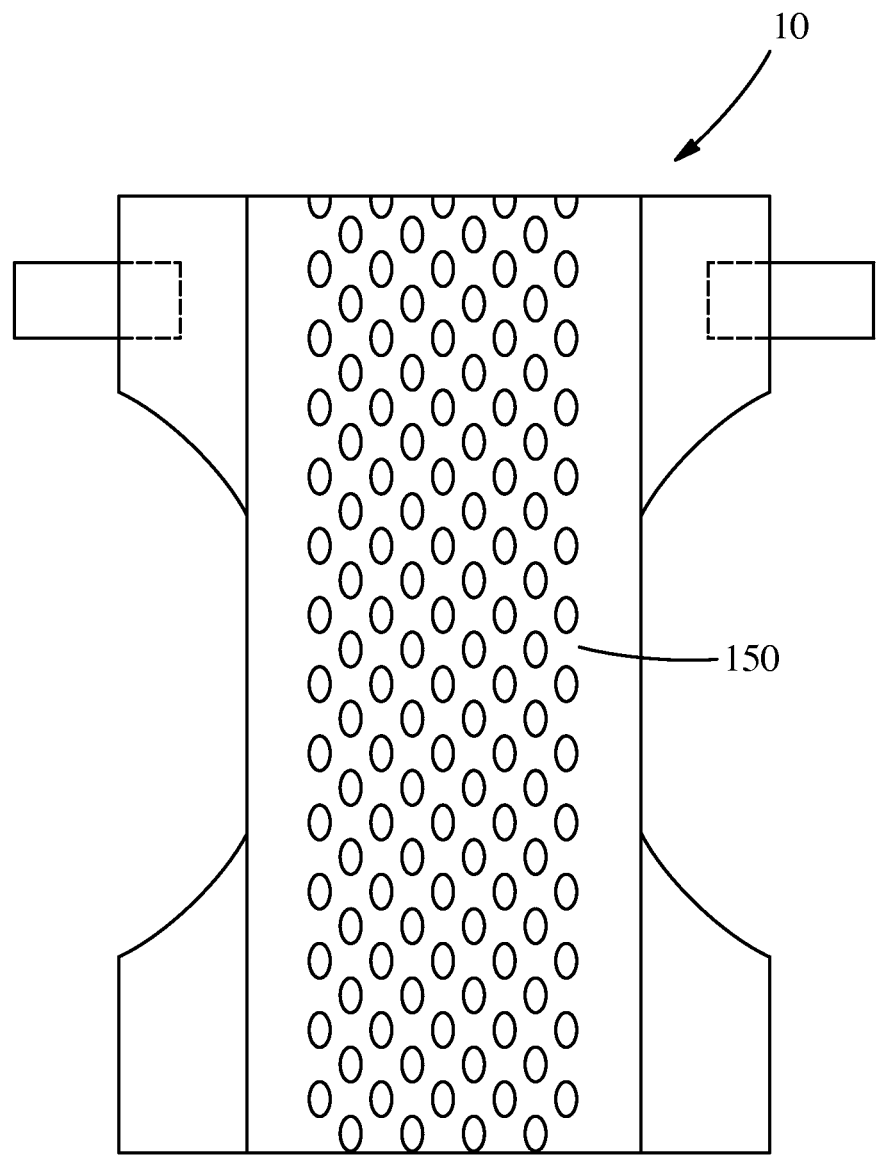
FIG. 5 is a plan view of a diaper as a preferred embodiment of an absorbent article according to the present invention.
Figure 5B:
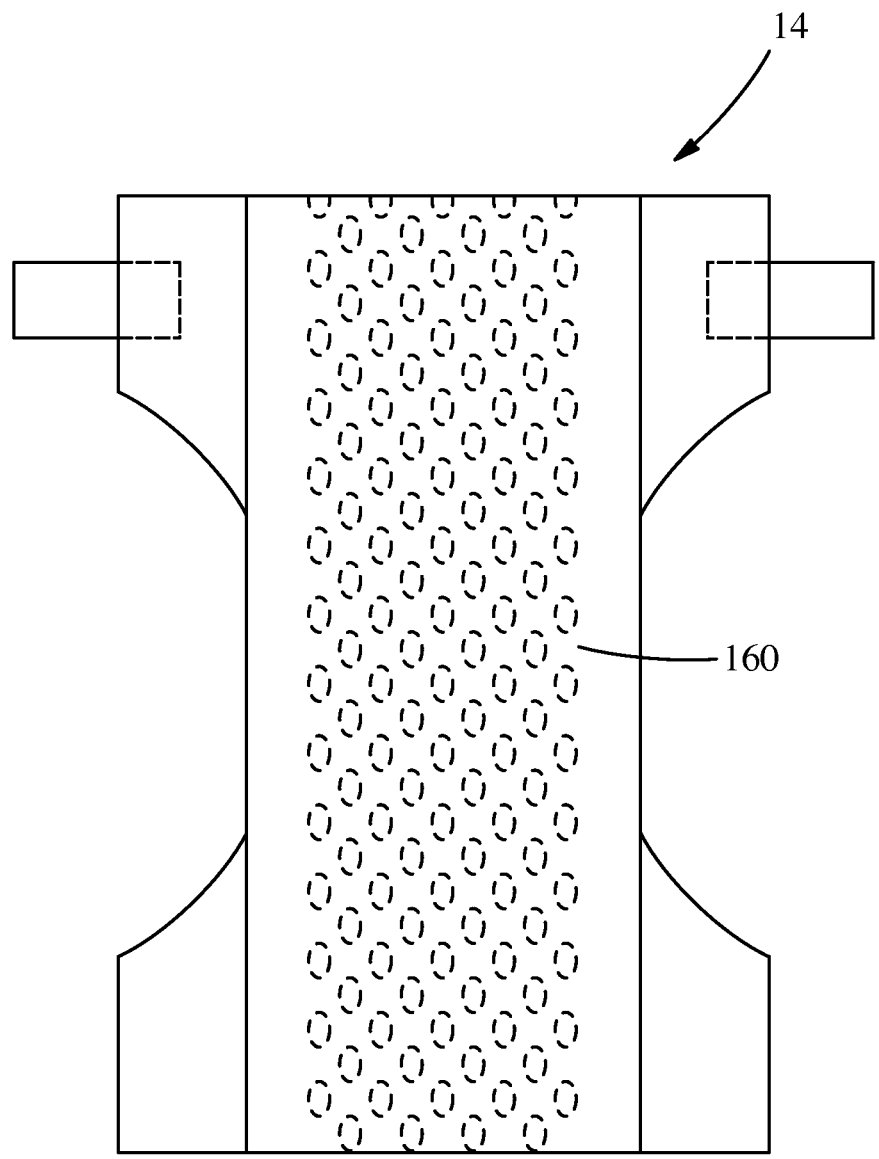

The interior design signal may be any pattern or shape which indicates absorbency to a caregiver. For purposes of illustration, FIG. 5 shows a design signal of a wavy design. Caregivers may consider a wavy design to connote a fluid motion, signaling absorbency. The wavy design/pattern may also create the appearance of absorption channels to distribute the liquid throughout the article. A network design/pattern may also be perceived to promote absorbency, as it indicates that liquid will dissipate more quickly through interconnected channels than straight channels. Thus, the network pattern indicates a controlled flow and distribution. Further, patterns or designs with teardrops may signal a benefit of containment, since the design/pattern is related to water/liquid and creates the appearance of absorption channels to distribute the liquid throughout the article.

In addition, any pattern may be utilized which helps communicate a product benefit to the consumer. Channels of absorption and systems of absorption may be visualized on the topsheet via interior design signals. Thus, designs/patterns may be connected or joined. Designs/patterns may be interrupted or continuous. Also, in order to enhance freedom of movement perception, patterns may communicate flexibility.

Channels of absorption, microfibers of gel, and multiple systems of absorption may be visualized via interior design signals, which may translate how the liquid will flow into the absorbent core of the article. Thus, the design cue may signal to the consumer that the graphics are a representation of what is happening "inside" the article. Further, the interior design signal may match the pattern of the absorbent polymer distributed in the core of the article.

Figure 6:
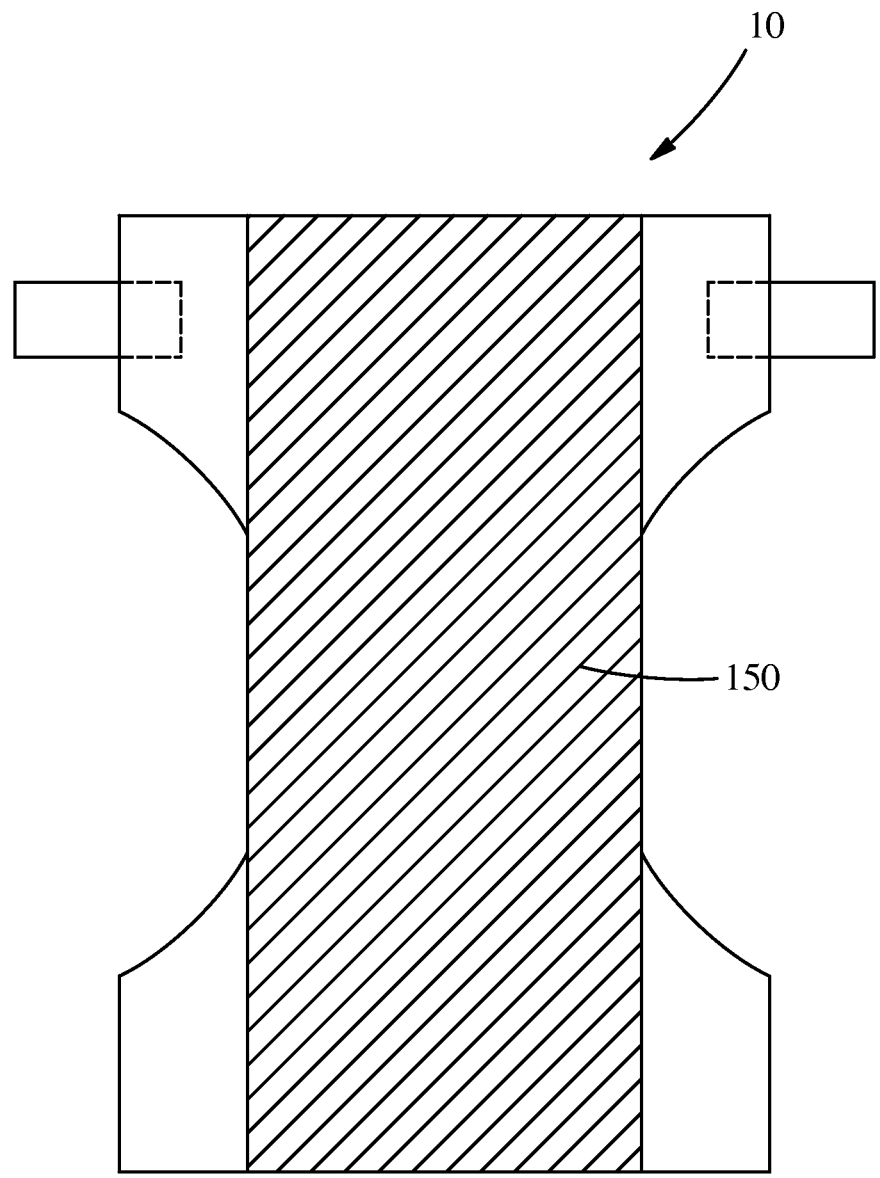
FIG. 6 is a plan view of a diaper as a preferred embodiment of an absorbent article according to the present invention.

The interior design signal of the present invention may also be a solid color. A visible layer of solid color may lead the caregiver to understand that the core is composed of several layers that perform complementary functions in absorbency. For instance, in one embodiment, the topsheet may be a solid color. In another embodiment, the layer directly below the topsheet may be a solid color. In another embodiment, any layer below the topsheet may be a solid color. In another embodiment, two or more layers may be a solid color. If two or more solid colors are used, they may complement each other or contrast each other. FIG. 6 is a plan view of another embodiment of diaper 20 according to the present invention.

The interior design signal may also be created by mechanically modifying the topsheet and/or another layer of the absorbent article. Preferred mechanisms of mechanical modification include, but are not limited to, embossing, slitting, creating overbonds that open up upon stretching, CPW bonding, ultrasonic bonding, heat bonding, and activation. In all of the mechanisms for mechanical modification, the material may be permanently deformed, broken, attached to another material, molten, and/or the surface (roughness) of the material may be changed. Accordingly, in addition to the position of the material, the opacity, brightness, gloss, and color of the material and the absorbent article at the treated areas may change. Those changes may be used to create an interior design signal.

The mechanical treatment that creates the interior design signal may be applied to a material (e.g. the topsheet or any other layer) prior to assembling the absorbent article. Alternatively, the mechanical treatment may be performed during assembling the absorbent article, or it may be applied after the absorbent article has been assembled.

For example, creating the interior design signal via embossing may be achieved during assembly of the absorbent article, after the topsheet has been combined with the absorbent core. The core/topsheet combination may be fed between two rolls pressed together with high pressure. One roll may have a flat surface and the other (embossing roll) may have the pattern engraved that is intended to be embossed.

Also, for example, creating the signal via slitting or creating overbonds that open up upon stretching, may be achieved via feeding the topsheet through two rolls. One roll may have sharp teeth of about the dimensions of the desired slits or overbonds that open up upon stretching, and the other roll may have valleys at the position opposing the teeth. One or both of the rolls may be heated and/or cooled. It may be desired to create slits or overbonds that open up upon stretching without sharp edges; this may be achieved by controlling the temperature of the rolls. The direction of the slits or overbonds that open up upon stretching may be in the machine direction, in the cross direction, or in any other relevant direction.

It may be desirable to create a random pattern of slits or overbonds that open up upon stretching. Alternatively, it may be desirable to have the slits or overbonds that open up upon stretching ordered, for instance, in a lattice configuration.

After creating the slits or overbonds that open up upon stretching, it may be desirable to further stretch the topsheet or other layer in the machine direction and/or in the cross direction. Stretching the topsheet or other layer in the cross direction that has regularly ordered slits or overbonds that open up upon stretching oriented in the machine direction creates a three dimensional structure with "open holes." This three dimensional structure with open holes may be a signal for caregivers, indicating that the absorbent article is very absorbent and can quickly absorb large quantities.

The interior design signal may continue from the very front of the article to the very back of the article. Further, the design signal may continue from side to side. Having an interior design signal that is distributed all along the article may indicate that the thin product will work due to liquid distribution and absorption taking advantage of the entire article. The interior design signal may be present on greater than about 40% of the length of the absorbent article, greater than about 50%, greater than about 60%, greater than about 70%, greater than about 80%, greater than about 90% of the length of the absorbent article. The length is measured measurement from the first edge 100 to the second edge 110 of the diaper. Further, the interior design signal may be present on greater than about 40% of the width of the absorbent article, greater than about 50%, greater than about 60%, greater than about 70%, greater than about 80%, greater than about 90% of the width of the absorbent article. The width is the distance between leg cuffs 24.

The interior design signal may be any color. The term "color" as referred to herein include any primary color, i.e., white, black, red, blue, violet, orange, yellow, green, and indigo as well as any declination thereof or mixture thereof within the CIELAB color space or scale. In the CIELAB space, a color may be defined by three parameters L*, a* and b* where L* represents luminance or lightness (0=black, 100=white), a* and b* independently each represent a two color axis, a* representing a red/green axis (+a=red, −a=green), while b* represents a yellow/blue axis (+b=yellow, −b=blue). (Commission Internationale d'Eclairage, 1976 L*, a*, b* color scale, i.e. CIELAB). Preferred colors for the present invention are those falling in the family of blues and greens, as defined by the CIELAB space. Blue and green interior design signals indicate absorbency to the consumer, as well as skin protection and skin health.

The interior design signal may also indicate that the absorbent article is absorbent after a wetness event. When wet, the interior design signal may become a darker color, thus, a visual signal indicating absorption to the caregiver.

Caregivers may have more confidence in a thin product with interior design signals versus a thin product without signals.

Ten caregivers were asked to rank order two separate sets of four diaper products which they believe to be the most absorbent to the least absorbent based only on looking at the inside of the diaper. The diapers were mounted on curved forms, and the caregivers were not allowed to feel the product. Thus, the ranking of the product's absorbency preference was based only on the interior design signal.

In the first set of four products, three of the four products included an interior design signal of a printed pattern having a wavy design, indicating channeling. One product had no pattern printed on it, and it displayed a white topsheet; this product is shown in the table below as "0% signal". Of the three products including an interior design signal, one product had 40% of the length covered in the pattern (shown below as "40% signal"); another product had 70% of the length covered in the pattern (shown below as "70% signal"); another product had 100% of the length covered in the pattern (shown below as "100% signal"). In the 40% signal and 70% signal examples, the portion of the product not showing a signal (the remaining 60% and 30% respectively) was a white topsheet. The percentage of length covered is based on a measurement from the first edge 100 to the second edge 110 of the diaper. In all of the products displaying the printed pattern, the entire width of the interior was covered. The entire width includes the portion of the interior diaper between the leg cuffs 24.

In ranking the products, the caregivers were told to rank 1 for most absorbent; 2 for second most absorbent; 3 for third most absorbent; and 4 for fourth most absorbent. Thus, an average ranking closer to 1 indicates more absorbent, and an average ranking closer to 4 indicates less absorbent.

Interior Design Signal - Printed Pattern

| % Signal | Code | Average Ranking | Std. Dev. | Sig @ 95% |
|---|---|---|---|---|
| 0% | E | 2.70 | 1.34 | — |
| 40% | P | 3.10 | 0.88 | — |
| 70% | M | 2.60 | 0.70 | — |
| 100% | A | 1.60 | 1.07 | MPE |

Thus, the diaper having 100% coverage by the interior design signal is rated to be significantly more absorbent than all other products.

In the second set of four products, three of the four products included an interior design signal of a solid color (periwinkle) layer that is placed under the topsheet layer. One product had no solid color exposed, and it displayed a white topsheet; this product is shown in the table below as "0% signal". Of the three products including an interior design signal, one product had 40% of the length covered in the solid color (shown below as "40% signal"); another product had 70% of the length covered in the solid color (shown below as "70% signal"); another product had 100% of the length covered in the solid color (shown below as "100% signal"). In the 40% signal and 70% signal examples, the portion of the product not showing a signal (the remaining 60% and 30% respectively) was a white topsheet. The percentage of length covered is based on a measurement from the first edge 100 to the second edge 110 of the diaper. In all of the products displaying the solid color, the entire width of the interior was covered. The entire width includes the portion of the interior diaper between the leg cuffs 24.

In ranking the products, the caregivers were told to rank 1 for most absorbent; 2 for second most absorbent; 3 for third most absorbent; and 4 for fourth most absorbent. Thus, an average ranking closer to 1 indicates more absorbent, and an average ranking closer to 4 indicates less absorbent.

Interior Design Signal - Solid Color (Periwinkle)

| % Signal | Code | Average Ranking | Std. Dev. | Sig @ 95% |
|---|---|---|---|---|
| 0% | C | 3.50 | 0.97 | — |
| 40% | L | 2.80 | 0.79 | — |
| 70% | S | 2.30 | 0.95 | C |
| 100% | H | 1.40 | 0.70 | CLS |

Thus, the diaper having 100% coverage by the interior design signal is rated to be significantly more absorbent than all other products. Further, the diaper having 70% coverage by the interior design signal is rated to be significantly more absorbent than the product with no interior design signal.

The interior design signals described herein may be used on any absorbent article. One preferred embodiment includes, but is not limited to, articles described in U.S. Patent Application No. 2004/0162536 and U.S. Patent Application No. 2004/0167486. The aforementioned applications are directed to absorbent articles having an absorbent core which imparts increased wearing comfort to the article and makes it thin and dry.

Wet Immobilization Test

Equipment

Graduated fluid beaker
Stop watch
Scissors
Light Box
Pen
Test solution: 0.90% saline solution at 37° C.
Metal ruler traceable to NIST, DIN, JIS or other comparable National Standard
PVC/metal dishes with a flat surface inside and a minimum length of the core bag length (n) to be measured and a maximum length n+30 mm, width of 105±5 mm, height of 30-80 mm or equivalent
Electronically spring-balance 0-50 kg (Type CH 50 K 50)
Wet Immobilization Impact Tester Equipment (WAIIT), Design package number: BM-00112.59500-R01 available from T.M.G. Technisches Buero Manfred Gruna Facilities: Standard laboratory conditions, temperature: 23° C.±2° C., relative humidity: max 55%

Sample Preparation a) Continuous (uncut) core:
  1. With scissors, cut off the core bags from the continuous web; cut in the middle of the absorbent core free area.
  2. Continue with "Sample Preparation All Products" below.

b) Finished product with floating cores:
  1. With scissors, cut off the poly-backsheet. Do not cut in the core bag. Only where the poly-backsheet is glued to the core bag, the poly-backsheet cannot be moved.
  2. Continue with "Sample Preparation All Products" below.

c) Finished Product without floating cores:
  1. Open the product, topsheet side up.
  2. Unfold the diaper and cut the cuff elastics approximately every 2.5 cm (a thumb width) to avoid chassis tension.
  3. For pull-up products only, open the side seams and remove the waistbands.
  4. For pull-up products only, cut the barrier leg cuff elastic approximately every 2.5 cm (a thumb width), but just 1 cm in depth so that both elastics are cut. For the leg elastics, cut the elastic so that both elastics are cut to avoid any contraction.
  5. Continue with "Sample Preparation All Products" below.

Sample Preparation all Products

1. Lay the core bag flat and rectangular topsheet side up onto the light box surface without any folds.
2. Switch on the light box to clearly identify the absorbent core outer edges.
3. With a ruler, draw a line at the front and back absorbent core outer edges.
4. Measure the distance (A), between the two markers and divide the value by 2, this will be calculated distance (B).
5. Measure the calculated distance (B) from front marker towards the middle of the core bag and mark it. At this marker draw a line in the cross direction.

Test Procedure

WAIIT Calibration:
  1. Make sure that the sliding board is in the lower position. Open the front door of the WAIIT tester and connect the spring-balance hook to the upper sample clamp of the WAIIT. Make sure that the clamp is closed before connecting the spring-balance.
  2. Use both hands on the spring-balance to lift continuously and as slowly as possible up the sliding board towards the upper position. Record the average value ($m_1$) during the execution to the nearest 0.02 kg.
  3. Guide down the sliding board as slowly as possible to the lower position and record the average value ($m_2$) read off during execution to the nearest 0.02 kg.
  4. Calculate and report the delta of $m_1$-$m_2$ to the nearest 0.01 kg. If the delta is 0.6 kg±0.3 kg continue measurement. Otherwise, an adjustment of the sliding board is necessary. Make sure that the sliding board is in lower position and check the sliding path for any contamination or damage. Check if the position of the sliding board to the sliding path is correctly adjusted by shaking the board. For easy gliding some clearance is needed. If not present, readjust the system.

WAIIT Test Settings:

Drop height is 50 cm.
Diaper load ($l_D$) is 73% of the core capacity (cc); $l_D$=0.73×cc.
Core capacity (cc) is calculated as: cc=$m_{SAP}$×$SAP_{GV}$, where $m_{SAP}$ is the mass of superabsorbent polymer (SAP) present in the diaper and $SAP_{GV}$ is the free swelling capacity of the superabsorbent polymer. Free swelling capacity of the superabsorbent polymer is determined with the method described in WO 2006/062258. The mass of the superabsorbent polymer present in the diaper is the average mass present in ten products.

Test Execution:
  1. Reset the balance to zero (tare), put the dry core bag on the balance, weigh and report it to the nearest 0.1 g.
  2. Measure the appropriate volume Saline (0.9% NaCl in deionized water) with the graduated cylinder.
  3. Lay the core bag, topsheet side up, flat into the PVC dish. Pour the saline evenly over the core bag.
  4. Take the PVC dish and hold it slanting in different directions, to allow any free liquid to be absorbed. Products with poly-backsheet need to be turned after a minimum waiting time of 2 minutes so that liquid under the backsheet can be absorbed. Wait for 10 minutes (+/−1 minute) to allow all saline to be absorbed. Some drops may retain in the PVC dish. Use only the defined PVC/metal dish to guarantee homogenous liquid distribution and less retained liquid.
  5. Reset the balance to zero (tare), put the wet core bag on the balance. Weigh and report it to the nearest 0.1 g. Fold the core bag just once to make it fit on the balance. Check to see if the wet core bag weight is out of limit (defined as "dry core bag weight+theoretical load±4 ml"). For example, 12 g dry core bag weight+150 ml load=162 g wet core bag weight. If the actual wet weight on the scale is between 158 g and 166 g, the pad can be used for shaking. Otherwise scrap the pad and use the next one.
  6. Take the loaded core bag and cut the pad along the marked line in the cross direction.
  7. Put the back of the wet core bag onto the balance ($m_1$). Weigh and report it to the nearest 0.1 g.

8. Take the wet core and clamp the end seal side up into the WAIIT. Make sure that the product is fixed to the sample holder along the whole product length. Make sure not to clamp the absorbent core, only the nonwoven; for pull-up products, use only the barrier leg cuff.
9. Lift up the sliding board to the upper position by using both hands until the board is engaged.
10. Close the safety front door and release the slide blade.
11. Reset the balance to zero (tare), take the tested core bag out of the WAIIT and put it on the balance ($m_2$). Report the weight to the nearest 0.1 g.
12. Repeat steps 7 to 11 with front of the wet core bag.

Reporting:
1. Record the dry core bag weight to the nearest 0.1 g.
2. Record the wet weight before ($m_{1\ front/back}$) and after ($m_{2\ front/back}$) testing, both to the nearest 0.1 g.
3. Calculate and report the average weight loss ($\Delta m$) to the nearest 0.1 g: $\Delta m = (m_{1front} + m_{1back}) - (m_{2front} + m_{2back})$
4. Calculate and report the weight loss in percent to the nearest 1%, ($\Delta m_{rel}$): $(\Delta m_{rel}) = (((m_{1front} + m_{1back}) - (m_{2front} + m_{2back})) \times 100) / (m_{1front} + m_{1back})$
5. Calculate and report Wet Immobilization (WI) as: $WI = 100\% - \Delta m_{rel}$ All documents cited in the Detailed Description of the invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

While particular embodiments of the present invention have been illustrated and described, it would be obvious to those skilled in the art that various other changes and modifications can be made without departing from the spirit and the scope of the invention. It is therefore intended to cover in the appended claims all such changes and modifications that are within the scope of this invention.

What is claimed is:

1. A disposable absorbent article comprising:
   a. an interior design signal comprising channels of absorption; and
   b. absorbent core including a first absorbent layer, the first absorbent layer including a first substrate, the first absorbent layer further including absorbent particulate polymer material deposited on the first substrate and thermoplastic material covering the absorbent particulate polymer material on the first substrate;
   c. wherein the interior design signal is located on a layer beneath a topsheet of the absorbent article and wherein the interior design signal is also located on the topsheet of the absorbent article;
   d. wherein the interior design signal is the pattern formed by the absorbent particulate polymer material distributed in the absorbent core.

2. The disposable absorbent article of claim 1, further comprising a second absorbent layer, the second absorbent layer including a second substrate, the second absorbent layer further including absorbent particulate polymer material deposited on the second substrate and thermoplastic material covering the absorbent particulate polymer material on the second substrate; the first and second absorbent layers combined together such that at least a portion of the thermoplastic material of the first absorbent layer contacts at least a portion of the thermoplastic material of the second absorbent layer, the absorbent particulate polymer material is disposed between the first and second substrates in an absorbent particulate polymer material area, and the absorbent particulate polymer material is substantially continuously distributed across the absorbent particulate polymer material area.

3. The disposable absorbent article of claim 2, wherein the absorbent particulate polymer material deposited on the first and second substrates forms on each substrate, a grid pattern comprising land areas and junction areas between the land areas, the junction areas containing little or no absorbent particulate polymer material.

4. The disposable absorbent article of claim 1, wherein the interior design signal matches the pattern of absorbent particulate polymer material deposited on the first substrate.

5. The disposable absorbent article of claim 2, wherein the interior design signal matches the pattern of absorbent particulate polymer material deposited on the first and second substrates.

6. The disposable absorbent article of claim 1, wherein the interior design signal is created by mechanically modifying the absorbent core.

7. The disposable absorbent article of claim 1, wherein the interior design signal further comprises patterns or solid colors.

8. The disposable absorbent article of claim 1, wherein the interior design signal is the same on the topsheet and the pattern formed by the absorbent particulate polymer material distributed in the absorbent core 9. The disposable absorbent article of claim 1, wherein at least the topsheet comprises a solid color.

10. The disposable absorbent article of claim 1, wherein at least a layer beneath the topsheet comprises a solid color, wherein the solid color is visible through the topsheet.

11. The disposable absorbent article of claim 1, further comprising an interior design signal on the leg cuffs.

12. The disposable absorbent article of claim 1, wherein the absorbent particulate polymer material may be immobilized when wet such that the absorbent core achieves a wet immobilization of greater than about 50%.

13. The disposable absorbent article of claim 1, wherein the absorbent particulate polymer material is present in the absorbent core in an amount of greater than about 80% by weight of the absorbent core.

14. The disposable absorbent article of claim 1, wherein the disposable absorbent article is a diaper.

* * * * *